(12) United States Patent
Aadal Nielsen et al.

US009513279B2

(10) Patent No.: US 9,513,279 B2
(45) Date of Patent: *Dec. 6, 2016

(54) INSECT-BASED EX VIVO MODEL FOR TESTING BLOOD-BRAIN BARRIER PENETRATION AND METHOD FOR EXPOSING INSECT BRAIN TO NANOPARTICLES

(75) Inventors: Peter Aadal Nielsen, Oxie (SE); Gunnar Andersson, Roestaanga (SE); Olga Andersson, Roestaanga (SE)

(73) Assignee: N2MO A/S, København S (DK)

( * ) Notice: Subject to any disclaimer, the term of this patent is extended or adjusted under 35 U.S.C. 154(b) by 85 days.

This patent is subject to a terminal disclaimer.

(21) Appl. No.: 13/881,566

(22) PCT Filed: Sep. 30, 2011

(86) PCT No.: PCT/DK2011/050367
§ 371 (c)(1),
(2), (4) Date: Jun. 7, 2013

(87) PCT Pub. No.: WO2012/055412
PCT Pub. Date: May 3, 2012

(65) Prior Publication Data
US 2014/0154725 A1 Jun. 5, 2014

(30) Foreign Application Priority Data
Oct. 25, 2010 (DK) .................................. 2010 00969

(51) Int. Cl.
*G01N 33/50* (2006.01)
(52) U.S. Cl.
CPC ...... *G01N 33/5058* (2013.01); *G01N 33/5085* (2013.01)
(58) Field of Classification Search
None
See application file for complete search history.

(56) References Cited

U.S. PATENT DOCUMENTS

2005/0132425 A1  6/2005  Lowe et al.
2008/0025959 A1  1/2008  Daneman et al.

FOREIGN PATENT DOCUMENTS

WO   WO 2004/006854 A2   1/2004
WO   WO 2010/031794      3/2010

OTHER PUBLICATIONS

Stork et al., Organization and Function of the Blood-Brain Barrier in *Drosophila*, The Journal of Neuroscience, 28(3):587-597, Jan. 16, 2008.*
Michaelis et al., Covalent Linkage of Apolipoprotein E to Albumin Nanoparticles Strongly Enhances Drug Transport into Brain, The Journal of Pharmacology and Experimental Therapeutics, 317:1246-1253, 2006.*
Gullan et al., The Insects: An Outline of Entomology, pp. 30-37, 56-58, Third Edition, Blackwell Publishing, 2005.*
Nielsen_DDT, Nielsen et al., Models for predicting blood-brain barrier permeation, Drug Discovery Today, vol. 16, Nos. 11/12, Jun. 2011.*
Carlson et al., "Blood Barriers of the Insect", *Annu. Rev. Entomol.*, vol. 45, 2000, pp. 151-174.
Garberg et al., "In vitro models for the blood-brain barrier", *Toxicology in Vitro*, vol. 19, 2005, pp. 299-334.
Josserand et al., "Evaluation of Drug Penetration into the Brain: A Double Study by in Vivo Imaging with Positron Emission Tomography and Using an in Vitro Model of the Human Blood-Brain Barrier", *The Journal of Pharmacology and Experimental Therapeutics*, vol. 316, No. 1, pp. 79-86, 2005.
Mayer et al., "Evolutionary Conservation of Vertebrate Blood-Brain Barrier Chemoprotective Mechanisms in *Drosophila*", *The Journal of Neuroscience*, vol. 29, No. 11, 2009, pp. 3538-3550.
International Search Report from International Application No. PCT/DK2011/050367 filed Jan. 16, 2012.
Khan et al., "Novel Model to Study Virulence Determinants of *Escherichia coli* K1", *Infection and Immunity*, vol. 75, No. 12, 2007, pp. 5735-5739.
Mokri-Moayyed et al., "Development of a novel ex vivo insect model for studying virulence determinants of *Escherichia coli* K1", *Journal of Medical Microbiology*, vol. 57, 2008, pp. 106-110.
Sarantseva et al., "Protein Transduction Domain Peptide Mediates Delivery to the Brain via the Blood-Brain Barrier in *Drosophila melanogaster* ", *Biochemistry (Moscow) Supplement Series B: Biomedical Chemistry*, vol. 3, No. 2, 2009, pp. 149-155.
Form PCT/ISA/210, International Search Report, for International Application PCT/EP2009/062023, dated Dec. 7, 2009.
Form PCT/ISA/220, Notification of Transmittal of the International Search Report and the Written Opinion of the International Searching Authority, for International Application PCT/EP2009/062023, dated Dec. 22, 2009.
Form PCT/ISA/237, Written Opinion, for International Application PCT/EP2009/062023, dated Apr. 2007.
Fortini et al., "Modeling human neurodegenerative diseases in *Drosophilia*," *TIG* (2000) 16 (4): 161-167.
Marsh et al., "Can files help humans treat neurodegenerative diseases?" *BioEssays* (2004) 26: 485-496.
Marsh et al., "*Drosophilia* in the study of neurodegenerative disease," *Neuron* (2006) 52: 169-178. XP002557534.
Parker et al., "Roles of glia in the *Drosophilia* nervous system," *Seminars in Cell & Developmental Biology*. (2006) 17: 66-77.
Wolf et al., "Invertebrate models of drug abuse," *J. Neurobiol.* (2003) 54: 161-178.

(Continued)

*Primary Examiner* — Taeyoon Kim
*Assistant Examiner* — Srikanth Patury
(74) *Attorney, Agent, or Firm* — Merchant & Gould P.C.

(57) ABSTRACT

There is provided an ex-vivo insect screening model to accurately determine blood-brain barrier penetration of different nanoparticles in order to improve the compound screening procedures/processes in the early drug discovery process. This object offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase.

6 Claims, No Drawings

(56) References Cited

OTHER PUBLICATIONS

Mortazavi et al., "Acanthamoeba produces disseminated infection in locusts and traverses the locust blood-brain barrier to invade the central nervous system", BMC Microbiology (2010), 10:186, 9 pages.
Hamamoto et al., "Silkworm as a model animal to evaluate drug candidate toxicity and metabolism", Comparative Biochemistry and Physiology, Part C, 149 (2009), 334-339.
He et al., "Benzo(a)pyrene toxicokinetics in the cricket following injection into the haemolymph", Environmental Toxicology and Pharmacology 6 (1998), 81-89.
Johny et al., "New Insect System for Testing Antibiotics", The Journal of Parasitology, vol. 93, No. 6, Dec. 2007, pp. 1505-1511.
Juang et al., "A blood-brain barrier without tight junctions in the fly central nervous system in the early postembryonic stage", Cell & Tissue Research (1992), 270: 95-103.
PCT/ISA/237, International Preliminary Report on Patentability, Written Opinion, PCT/DK2011/050367, dated Jul. 2011.
Khan et al., "Novel Model to Study Virulence Determinants of *Escherichia coli* K1," Infection and Immunity, vol. 75, No. 12 (Jan. 12, 2007), pp. 5735-5739.
Mokri-Moayyed et al., "Development of a novel ex vivo insect model for studying virulence determinants of *Escherichia coli* K1,"Journal of Medical Microbiology, vol. 57 (2008), pp. 106-110.

\* cited by examiner

INSECT-BASED EX VIVO MODEL FOR TESTING BLOOD-BRAIN BARRIER PENETRATION AND METHOD FOR EXPOSING INSECT BRAIN TO NANOPARTICLES

This application is a National Stage Application of PCT/DK2011/050367, filed 30 Sep. 2011, which claims benefit of Serial No. PA 2010 00969, filed 25 Oct. 2010 in Denmark and which applications are incorporated herein by reference. To the extent appropriate, a claim of priority is made to each of the above disclosed applications.

FIELD OF THE INVENTION

The present invention is directed to insect models that are aimed to reflect vertebrate blood-brain barrier (BBB) penetration of nanoparticles. On the other hand BBB penetration of nanoparticles may also cause side effects. Specifically, the present invention relates to the use of insects in screening for BBB penetration of nanoparticles.

BACKGROUND OF THE INVENTION

Although there are anecdotal data indicating a causal relationship between long-term ultrafine particle exposures in ambient air (e.g., traffic related) or at the workplace (e.g., metal fumes) and resultant neurotoxic effects in humans, more studies are needed to test the hypothesis that inhaled nanoparticles (NP) or NPs absorbed via food cause neurodegenerative effects. Some NPs may have a significant environmental safety (hazard) potential, and this will pose a significant risk if there is a sufficient exposure. The challenge is to identify such hazardous NPs and take appropriate measures to prevent exposure.

It has been shown that certain NPs do permeate the BBB and in this relation it is important that the NPs are readily cleared from the brain such that the NPs do not cause any brain damage. Hindering the NP from entering the brain is not straight forward since the mechanism describing how the NPs permeate the BBB still is under debate. However, it is of utmost importance to identify NPs that permeate the BBB in order to address potential toxicological issues or to use the NP as carrier of a drug.

In relation to fighting CNS brain disorders NPs have shown promising as carriers of drugs that could not otherwise have passed the blood brain barrier. Despite enormous advances in brain research, CNS brain disorders still remain accountable for a high number of hospitalizations requiring prolonged care. It is estimated that approximately 1.5 billion people worldwide are suffering from various CNS disorders, such as Alzheimer's disease, Parkinson's disease, amyotrophic lateral sclerosis, multiple sclerosis, HIV-dementia and stroke, among others.

The blood-brain barrier (BBB) has always presented a challenge to scientists for brain drug targeting. The BBB has evolved in such a way that it protects the brain from various foreign substances such as neurotoxins. This mechanism makes the BBB an insurmountable barrier for numerous highly essential drugs, including antibiotics, cytostatics and other CNS-active drugs.

Many strategies have been developed to overcome the hurdles caused by the BBB. They include both invasive and noninvasive approaches. The invasive approaches include the temporary disruption of the BBB, which allows the entry of drugs to the brain, and direct drug delivery to the brain by means of intraventricular or intracerebral injections, and intracerebral polymeric implants. The noninvasive approaches use colloidal drug carriers.

Among the non-invasive approaches, polymeric nanoparticles, especially poly(butylcyanoacrylate) (PBCA) nanoparticles coated with polysorbate 80, have recently received much attention from neuroscientists as an attractive and innovative carrier for brain targeting. These nanoparticles may be defined as a submicron drug-carrier system, which are generally polymeric in nature. Since nanoparticles are small in size, they easily penetrate into small capillaries and can be taken up within cells, allowing efficient drug accumulation at targeted sites in the body. The first reported nanoparticles were based on non-biodegradable polymeric systems. Their use for systemic administration, however, could not be considered because of the possibility of chronic toxicity due to the tissue and immunological response towards the non-biodegradable polymer. Hence, nanoparticles prepared with biodegradable polymers such as poly (cyanoacrylate) were exclusively studied. The use of biodegradable materials for nanoparticle preparation allows sustained drug release at the targeted site over a period of days or even weeks after injection.

Investigation of BBB permeation of nanoparticles is extremely important since there is an increasing use of nanoparticles and the profile for many of these are yet to be understood. Moreover, nanoparticles are important in drug discovery as they have proven to be useful as carriers for potential CNS drugs. On the one hand successful CNS drugs have to cross the BBB. Certain insects may be suitable as model organisms for studying BBB penetration of NPs. Insects are multi cell organisms with complex compartmentalized nervous systems for specialized functions like vision, olfaction, learning, and memory. The nervous systems of the insects respond physiologically in similar ways as in vertebrates with many identical neurohormones and receptors. Insects have avascular nervous systems in which hemolymph bathes all outer surfaces of ganglia and nerves. Therefore, many insects require a sophisticated BBB system to protect their CNS from plant-derived neurotoxins and to maintain an appropriate ionic microenvironment of the neurons. In fact, also in insects a sophisticated BBB system has been an evolutionary advantage. In insects this BBB is mainly based on the glia cell system which certainly shifted to the endothelial system as a response to the increased importance of the microvasculature in the vertebrate brain. In support of this view is the appearance of the glia system in elasmobranch fish and the remnants of their glia barrier in modern mammalian CNS. Thus, insects possess a BBB which is an important component in the ensheathment of the nervous system. The BBBs in insects are highly sophisticated but varies in structure between different insect orders. Thus insects with highly sophisticated brain barriers with complex integrative components that mimic the vertebrate barriers will be excellent models for documentation of penetration of various molecules through this structure.

Thus, there is a need for efficient screening of NPs permeability of the BBB both in order to address the environmental safety of NP as well as identifying NPs that can be used as carriers of drugs targeting CNS related diseases. This screening is preferentially performed in insect models with intact BBB function and this will contribute to a positive selection of NPs that are non toxic to vertebrates.

SUMMARY OF THE INVENTION

The object of the present invention is to develop an ex-vivo insect screening model to accurately assess blood-brain barrier penetration of different NPs in order to improve the screening procedures/processes.

This object offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase. Finally, it is an object of the present invention that only the penetration trough the blood-brain barrier is determined, without any interference from liver metabolism, accumulation in other tissues etc.

Accordingly, there is provided a method of conducting blood-brain barrier penetration studies of a NP in an insect, said method comprising the steps:

optionally anesthetizing the insect;
fixing the head of the insect;
dissecting out the dorsal part of the insect head so as to expose the brain, eyes, antennas, and nerve associations;
treating the brain while in its cuticle shell with a solution of the NP; and
removing the brain from its cuticle;
washing and homogenising the brain; and
determining the concentration of the NP in the homogenised brain material.

In a preferred embodiment of the present invention albumin is added to the solution of the NP to introduce the plasma protein binding and the effect of the plasma protein binding upon the nanoparticle's BBB penetration (free vs. protein bound nanoparticles). Preferably, hemolymph from the insect is also added to the NP sample either alone or in combination with albumin. It may be necessary to add an anti-coagulation agent to the hemolymph.

In another preferred embodiment of the present invention hemolymph is added to the solution of the NP to introduce the plasma protein binding and the effect of the plasma protein binding upon the nanoparticle's BBB penetration (free vs. protein bound nanoparticles).

In yet another preferred embodiment of the present invention hemolymph and albumin is added to the solution of the NP to introduce the plasma protein binding and the effect of the plasma protein binding upon the nanoparticle's BBB penetration (free vs. protein bound nanoparticles).

Preferable the concentration of the NP is determined by LC/MS or ICP-MS. In this respect the determination of the concentration of the NP is performed by homogenizing or ultra sound disintegration (UD) of the dissected brains, and analyzing the concentration of the test agent in the homogenate by liquid chromatography with mass spectrometric detection of the eluted compounds, by ICP-MS or fluorescent microscopy.

In order to ensure optimum penetration of the NP, the brain is treated with a solution of the NP for a period of 1 min. to 2 weeks, preferably to 1 week, more preferably to 2 days, most preferably to 12 hours In a particularly preferred embodiment of the present invention the neural lamella of the brain is removed before the brain is subjected to the NP.

In addition to the method of the present invention there is further provided a model for conducting blood-brain barrier penetration studies of a NP, said model obtained by a method comprising the steps:

optionally anesthetizing an insect having a BBB;
fixing the head of the insect; and
dissecting out the dorsal part of the insect head so as to expose the brain, eyes, antennas, and nerve associations; and
optionally removing the neural lamella, which is surrounding the BBB;

In a preferred embodiment of the present invention the NPs are made less prone to aggregate. Thereby the NPs are also more easily taken up by macrophages (monocytes); this is referred to as opsonization and may be made by mixing the NPs with albumin, such as BSA, possibly in combination with hemolymph.

The method of the present invention permits the exposure to an insect brain of a NP at a stable concentration during the entire period of exposure. As appears from above the insect model used in the method consists of the dorsal part of the insect head dissected out to consist of the brain, eyes, antennas and the nerve associations between these sense organs. Still in its cuticle shell the brain will be treated with different NPs for various times. The penetration of the test NP over the BBB into the brain is determined as the concentration (amount) of the nanoparticle measured in the isolated brain and preferably determined by LC/MS or ICP-MS. Alternatively the BBB permeability may be determined by fluorescent microscopy. The model is aimed as an early stage test of NPs ability to pass the BBB at a well defined and constant exposure concentration.

Preferably the dissected brains are homogenized or disintegrated by ultra sound or other methods and eventually lysed in order to obtain a homogeneous liquid reflecting the composition of the brains. The liquid is centrifuged and the supernatant stored until analysis. The further analysis of the liquid may be performed by virtue of liquid chromatography, possibly with mass spectrometric detection of the eluted compounds.

Alternatively, the presence of NPs in the brain may be identified and quantified by histochemical methods.

In various aspects and embodiments the present invention provides the subject-matter set out in the claims below.

DETAILED DESCRIPTION OF THE INVENTION

The present invention provides a new methodology for screening nanoparticle's ability to penetrate the BBB. Certain NPs do permeate the BBB and in this relation it is important that the NPs are readily cleared from the brain such that the NPs do not cause any brain damage. Hindering the NP from entering the brain is not straight forward since the mechanism describing how the NPs permeate the BBB still is debated. However, it is of utmost importance to identify NPs that permeate the BBB in order address potential toxicological issues or to use the NP as carrier of a drug.

The invention is generally useful for investigating the safety profile of NPs including NPs developed in drug discovery programs targeting a variety of diseases and disorders, specifically degenerative disorders, including: Parkinson's Disease, Alzheimer's Disease, Huntington's Disease, Diseases with motor neuron inclusions, Tauopathies, Corticobasal degeneration Neuropsychiatric disorders, including: Depression Bipolar disease, Schizophrenia, Anxiety, Aggression and Brain tumors. Moreover, the invention is applicable for drug discovery programs targeting peripherical targets where no CNS driven side effect can be tolerated. Moreover, the present invention is applicable in the screening of agents developed in drug discovery programs targeting eating disorders and sleep disorders etc.

In preferred embodiments the nanoparticles of the present invention is less than 100 nm.

There are several methods for creating nanoparticles, including both attrition and pyrolysis. In attrition, macro or micro scale particles are ground in a ball mill or other size reducing mechanism. Thermal plasma can also deliver the energy necessary to cause evaporation of small micrometer size particles. Inert-gas condensation is frequently used to make nanoparticles from metals with low melting points. The metal is vaporized in a vacuum chamber and then supercooled with an inert gas stream. The supercooled metal vapor condenses into nanometer-sized particles, which can be entrained in the inert gas stream and deposited on a substrate or studied in situ.

The present invention relates to but is not restricted to the use of insects selected from the following orders: (Taxonomy according to: Djurens Värld, Ed B.Hanström; Förlagshuset Norden A B, Maölmö, 1964):

| Order | Suborder/family | Comment |
|---|---|---|
| Dictyoptera | Blattodea | Cockroach |
|  | Mantoidea |  |
| Orthoptera | Grylloidea | Crickets |
|  | Acridoidea | Grasshoppers |
| Cheleutoptera |  | Stick insects |
| Lepidoptera |  | Moths |
| Hymenoptera | Formicoidea | Ants |
|  | Vespoidea | Wasps |
|  | Apoidea | Bee like Hymenopterans |
|  | Bombinae | Bumble-bees |
|  | Apine | Proper bees |
| Odonata |  | Dragonflies |
| Diptera | Nematocera | Mosquitos |
|  | Brachycera | Flies E.g *Drosophila* |

In particular the invention relates to insect species selected from *Blattodea, Acridoidea, Cheleutoptera, Brachycera* and *Lepidoptera* and most particular *Acridoidea* (*Locusta migratoria* and *Schistocera gregaria*) are preferred.

The invention will also relate to the following orders comprising insect species relevant for the method of the present invention:

| Order | Suborder/family | Comment |
|---|---|---|
| Ephemerida |  | Mayflies |
| Plecoptera |  |  |
| Dermoptera | Forficuloidea | Earwigs |
| Homoptera | Cicadinea | Cicadas |
|  | Aphidine | Plant-louse |
| Heteroptera |  | Hemipteran |
| Coleoptera |  | Beetles |
| Trichoptera |  | Caddis fly |

Large insects, such as the migratoty locust, *Locusta migratoria* and the desert locust, *Schistocera gregaria* or cockroach where it is feasible to feed and inject drugs and subsequently take hemolymph samples and dissect brain tissues, for analyses are preferred. The locust has been used to develop screening models to determine BBB penetration of different NPs and compare this model with existing literature data from conventional in vivo or in situ vertebrate studies.

In accordance with a preferred embodiment the migratoty locust, *Locusta migratoria* and/or the desert locust, *Schistocera gregaria*, is used since it is easy to breed and it is a relatively large insect (40-60 mm long, weight: approx. 2 g, hemolymph volume: approx. 300 μL, brain weight: approx. 2 mg).

The application of nanoparticles to insects in a screening method may be as follows, in accordance with a preferred embodiment of the present invention.

EXAMPLES

1. In a preferred embodiment the insects are selected from the order *Acridoidea* and specifically *Locusta migratoria* and *Schistocera gregaria* are used. The insects may be obtained from local suppliers or bred in house. The grasshoppers were reared under crowded conditions at 28°-34° and a 12:12 dark:light photo cycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. This preparation in its cuticle shell is placed in a well of a microtitre plate containing the NP. After various times of exposure the preparation is washed in saline and the brain is dissected under microscope with fine forceps. The neural lamella surrounding the brain is removed in saline and the brain is then disintegrated and the sample is frozen until analyses. NP presence is analysed by HPLC, LC/MSMS, ICP-MS or other methods.

2. In a preferred embodiment the insects are selected from the order *Acridoidea* and specifically *Locusta migratoria* and *Schistocera gregaria* are used. The insects may be obtained from local suppliers or bred in house. The grasshoppers were reared under crowded conditions at 28°-34° and a 12:12 dark:light photo cycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. This preparation in its cuticle shell is placed in a well of a microtitre plate containing the NP. After various times of exposure the preparation is washed in saline and the brain is dissected under microscope with fine forceps. The neural lamella surrounding the brain is removed in saline and the brain is fixated and prepared for histology. The presence of NPs in the brain is analysed by fluorescense microscopy, ICP-MS or other methods.

3. In a preferred embodiment the insects are selected from the order *Acridoidea* and specifically *Locusta migratoria* and *Schistocera gregaria* are used. The insects may be obtained from local suppliers or bred in house. The grasshoppers were reared under crowded conditions at 28°-34° C. and a 12:12 dark:light photo cycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. The neural lamella is removed and the preparation placed in a well of a microtitre plate containing the NP and 4.2% bovine serum albumin. After various times of exposure the preparation is washed in saline. The brain is lysed and the samples are sent for analysis to determine the NP permeability by ICP-MS, microscopy or other methods.

4. In a preferred embodiment the insects are selected from the order *Acridoidea* and specifically *Locusta migratoria* and *Schistocera gregaria* are used. The insects may be obtained from local suppliers or bred in house. The grasshoppers were reared under crowded conditions at 28°-34° C. and a 12:12 dark:light photo cycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. The neural lamella is removed and the preparation placed in a well of a microtitre plate containing the NP in hemolymph and 4.2% bovine serum albumin. After various times of exposure the preparation is washed in saline. The brain is lysed and the samples are sent for analysis to determine the NP permeability by ICP-MS, microscopy or other methods.

5. In a preferred embodiment the insects are selected from the order *Acridoidea* and specifically *Locusta migratoria* and *Schistocera gregaria* are used. The insects may be obtained from local suppliers or bred in house. The grasshoppers were reared under crowded conditions at 28°-34° C. and a 12:12 dark:light photo cycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. The neural lamella is removed and the preparation placed in a well of a microtitre plate containing the NP and hemolymph. After various times of exposure the preparation is washed in saline. The brain is lysed and the samples are sent for analysis to determine the NP permeability by ICP-MS, microscopy or other methods.

6. In a preferred embodiment the insects are selected from the order *Acridoidea* and specifically *Locusta migratoria* and *Schistocera gregaria* are used. The insects may be obtained from local suppliers or bred in house. The grasshoppers were reared under crowded conditions at 28°-34° and a 12:12 dark:light photo cycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. The neural lamella is removed and the preparation placed in a well of a microtitre plate containing the NP. After various times of exposure the preparation is washed in saline. The brain is lysed and the samples are sent for analysis to determine the NP permeability by ICP-MS, microscopy or other methods.

In the following the present invention is exemplified in further detail.

Example A

A cut was made through the frontal part of the head of female locusts. Each brain in its cuticle was placed in a silver nanoparticle (SNP; 80 nm) solution for 3 hours. The brains were dissected in saline, the neural lamella removed, washed twice in saline and then placed in tubes containing 100 ul nitric acid. The average content of silver (Ag) per brain was 5.61 ng as measured by ICP-MS. Average background content of Ag in control brains was 0.36 ng per brain.

Example B

Locust brains were dissected in saline and the neural lamella removed. The brains were placed in a SNP (80 nm) solution for 3 hours. The brains were washed twice in saline and then placed in tubes containing 100 ul nitric acid. The average content of Ag per brain was 21.7 ng as measured by ICP-MS.

Example C

Locust brains were dissected in saline and the neural lamella removed. The brains were placed in solutions containing a fluorescent polystyrene amino modified 100 nm nanoparticle and exposed for 3 hours. There was a marked uptake in the locust brain barrier and also strong indications of a deterioration of the brain barrier.

CONCLUSION

Ex vivo modeling in the locust clearly indicate the utility of the model in studies of brain permeation with reference to nanoparticles with different chemical properties. The observations of effects on brain barrier integrity are of extraordinary importance since the effects of nanoparticles on brain barrier permeation due to functional deterioration is not fully understood.

REFERENCES

Abbott, N. J. 2005 Dynamics of CNS barriers: evolution, differentiation, and modulation. Cell Mol Neurobiol 25: 5-23

Andersson, G. et al (2010), Manuscript under preparation.

Daneman, R. and Barres, B. A. 2005 The blood-brain barrier; lessons from moody flies. Cell 123: 9-12

Di, L. and Kerns, E. H. (2003). Profiling drug-like properties in discovery research. *Current Opinion in Chemical Biology* 7, 402-408.

Gaertner, L. S., Murray, C. L., Morris, C. E. (1998). Transepithelial transport of nicotine and vinblastine in isolated malpighian tubules of the tobacco hornworm (*Manduca sexta*) suggests a P-glycoprotein-like mechanism. *The Journal of Experimental Biology* 201, 2637-2645.

Garberg, P. et al. (2005). In vitro models for the blood-brain barrier. *Toxicology in Vitro* 19, 299-334.

Löscher, W and Potschka, H 2005 Blood-brain barrier active efflux transporters: ATP binding cassette gene family. NeuroRx 2: 86-98

Mayer, F. et al., 2009 Evolutionary conservation of vertebrate blood-brain barrier chemoprotective mechanisms in Drosophila. J Neuroscience 29: 3538-3550.

Neuwelt, E. et al., 2008; Strategies to advance translation research into brain barriers. Lancet Neurol 7: 84-96.

Nitta, T. et al., 2003 Size-selective loosening of the blood-brain barrier in Claudine-5-deficient mice. J Cell Biol 161: 653-660.

Pardridge, W. M. (2002). Drug and gene targeting to the brain with molecular Trojan horses. *Nature Reviews Drug Discovery* 1, 131-139

Pardridge W. M., 2005 Molecular biology of the blood-brain barrier. Mol Biotechnol 30: 57-70.

Summerfield, S. G. et al., 2007. Central nervous system drug disposition: The relationship between in situ brain permeability and brain free fraction. J Pharmacol Exp Ther 322: 205-213

Schinkel, A. H. et al., 1997 Normal viability and altered pharmacokinetics in mice lacking mdr1-type (drug-transporting) P-glycoproteins. PNAS 94: 4028-4033.

Schinkel, A. H. (1999). P-Glycoprotein, a gatekeeper in the blood-brain barrier. *Advanced Drug Delivery Reviews* 36, 179-194.

Summerfield, S. G. et al. (2006). Improving the In Vitro Prediction of In Vivo CNS Penetration: Integrating Permeability, Pgp Efflux and Free Fractions in Blood and Brain. *J of Pharm Exp Ther.* 316: 1282-90.

Turksen, K. and Troy, T.-C. (2004). Barriers built on claudins. *Journal of Cell Science* 117, 2435-2447.

Xia, C. Q., Xiao, G., Liu, N., Pimprale, S., Fox, L., Patten, C. J., Crespi, C. L., Miwa, G., Gan, L.-S. (2006). Comparison of Species Differences of P-Glycoproteins in Beagle Dog, Rhesus Monkey, and Human Using ATPase Activity Assays. *Molecular Pharmaceutics* 3 (1), 78-86.

Wu V M and Beitel G J, 2004 A junctional problem of apical proportions: epithelial tube-size control by septate junctions in the Drosophila tracheal system. Curr Opin Cell Biol 16: 493-499.

Zlokovic, B. V. 2008 The blood-brain barrier in health and chronic neurodegenerative disorders. Neuron 57: 178-201.

The invention claimed is:

1. A method of conducting blood-brain barrier penetration studies of nanoparticles in an insect, said method comprising the steps:
    optionally anesthetizing the insect;
    fixing the head of the insect;
    dissecting out the dorsal part of the insect head so as to expose the brain, eyes, antennas, and nerve associations;
    optionally removing the neural lamella;
    treating the brain with an intact blood brain barrier (BBB) while the brain is in its cuticle shell ex vivo by incubating in a solution of the nanoparticles;
    washing and homogenising or ultra sound disintegrating the brain; and
    determining the concentration of the nanoparticles in the homogenised brain material.

2. The method of claim 1, wherein the penetration of the nanoparticles through the blood-brain barrier is calculated.

3. The method of claim 1, wherein hemolymph and/or albumin is added to the nanoparticles.

4. The method of claim 1, wherein the concentration of the nanoparticles is determined by liquid chromatography/mass spectrometry (LC/MS).

5. The method of claim 1, wherein the brain is treated with the nanoparticles for a period of 1 minute to 2 days.

6. The method of claim 1, wherein the neural lamella of the brain are removed before the brain is homogenised or ultra sound disintegrated.

\* \* \* \* \*